(12) United States Patent
Robinson

(10) Patent No.: US 6,390,988 B1
(45) Date of Patent: May 21, 2002

(54) METHOD AND APPARATUS FOR MEASURING PULMONARY BLOOD FLOW BY PULMONARY EXCHANGE OF OXYGEN AND AN INERT GAS WITH THE BLOOD

(76) Inventor: Gavin Joseph Brian Robinson, Burwood (AU)

( * ) Notice: Subject to any disclaimer, the term of this patent is extended or adjusted under 35 U.S.C. 154(b) by 0 days.

(21) Appl. No.: 09/530,084

(22) PCT Filed: Oct. 24, 1997

(86) PCT No.: PCT/AU97/00717

§ 371 Date: Jun. 27, 2000

§ 102(e) Date: Jun. 27, 2000

(87) PCT Pub. No.: WO98/18383

PCT Pub. Date: May 7, 1998

(51) Int. Cl.[7] ................................................. A61B 5/08
(52) U.S. Cl. ...................... 600/531; 600/529; 600/532; 128/204.18
(58) Field of Search ................................. 600/531, 529, 600/532, 533, 538, 504, 481, 484; 128/204.18, 204.21

(56) References Cited

U.S. PATENT DOCUMENTS

| | | |
|---|---|---|
| 4,363,327 A | 12/1982 | Clark |
| 4,607,643 A | 8/1986 | Bell et al. |
| 4,722,347 A * | 2/1988 | Abrams ....................... 600/437 |
| 5,005,582 A | 4/1991 | Serikov et al. |
| 5,588,424 A * | 12/1996 | Insler ..................... 128/207.15 |
| 5,660,175 A * | 8/1997 | Dayal ..................... 128/207.15 |
| 6,227,196 B1 * | 5/2001 | Jaffe et al. .................. 600/481 |

FOREIGN PATENT DOCUMENTS

EP 074 809 B1 11/1987

OTHER PUBLICATIONS

Sekins et al., "Hyperthermic Treatment of Lung Cancer—by Filling Preselected Pulmonary Air Passages with Liquid and Heating the Liquid Exogenously or with Ultrasound," *Derwent World Patent Index Accession No. 101875/199114*, 1991. Abstract of AU 74489/94.

Ruchkin and Vorontsov, "Pulmonary Blood Flow Quantity Test—by Supplying a Fixed Volume of of Admixture of Inert Gas at the Beginning of Each in Halation," *Derwent World Patent Index Accession No. 305756/198449*, 1984. Abstract of SU 1085588.

* cited by examiner

*Primary Examiner*—Eric F. Winakur
*Assistant Examiner*—Navin Natnithithadha
(74) *Attorney, Agent, or Firm*—Seed Intellectual Property Law Group PLLC (57) ABSTRACT

A method and apparatus for measuring pulmonary blood flow in a subject by pulmonary exchange of oxygen and an inert gas with the blood using a divided respiratory system. One method of isolating two or more divisions of the respiratory system uses a multi-lumen cuffed endobronchial catheter. In one embodiment, a triple-lumen cuffed endobronchial catheter is provided. In another embodiment, gas mixtures are supplied to each lumen using a bag-in-a-box type ventilator for each breathing system for synchronizing the rate and pressure of mixed gas supplied to the lumens.

27 Claims, 3 Drawing Sheets

METHOD AND APPARATUS FOR MEASURING PULMONARY BLOOD FLOW BY PULMONARY EXCHANGE OF OXYGEN AND AN INERT GAS WITH THE BLOOD

BACKGROUND

This invention relates to the measurement of blood flow in a subject, more particularly to a method and apparatus for measuring pulmonary blood flow by pulmonary exchange of oxygen and an inert gas with the blood utilising a divided respiratory system. The invention is especially suitable for monitoring pulmonary blood flow/cardiac output of a patient under general anaesthetic and accordingly it will be convenient to describe the invention in connection with this application. However, it is to be understood that the method and apparatus described herein may be used for determining the pulmonary blood flow or cardiac output of a subject in a conscious state.

The equation that links the cardiac output of a subject to more directly measured parameters is as follows:

$$\dot{U}_{gas} = \dot{Q}_c \lambda (F_{Agas} - F_{\bar{v}gas})$$

where $F_{Agas}$ refers to the concentration of inert soluble gas in the alveolar gas mixture of the lungs expressed as a fraction of its partial pressure to the barometric pressure (Bp), $F_{\bar{v}gas}$ refers to the fraction of the inert soluble gas in the mixed venous blood expressed as a fraction of its partial pressure to the total pressure, $\lambda$ is the Ostwald solubility coefficient of the inert soluble gas in blood, $\dot{Q}_c$ is the cardiac output that passes through the pulmonary capillaries in the walls of gas-containing alveoli, and $\dot{U}_{gas}$ is the uptake into the blood from the alveoli measured in units of volume at body temperature and barometric pressure per unit time.

This equation holds true for inert gases only. In this regard an inert gas dissolves in blood proportionally to its partial pressure i.e. it obeys Henry's Law. By contrast a reactive gas does not obey Henry's Law by reason of its reacting chemically with blood constituents. Oxygen and carbon dioxide are examples of reactive gases.

The term cardiac output as used herein refers to the amount of blood per unit time which passes through the pulmonary capillaries in the walls of the alveoli of the lungs. If haemoglobin $O_2$ saturation of the subject is 100% then the whole cardiac output will be equivalent to the pulmonary blood flow, i.e. the amount of oxygenated blood passing through the pulmonary capillaries in the walls of the alveoli of the lungs. If this saturation is less than 100% the whole cardiac output includes shunt blood in addition to pulmonary blood flow. Shunt blood does not transport $O_2$ from the lungs to the tissue and may therefore be ignored. The % shunt may be estimated from pulse oximetry.

Most methods in use today or described in the literature refer to or depend on the above equation, but $F_{\bar{v}gas}$ cannot be measured accurately without obtaining a sample of mixed venous blood, which would sacrifice the advantage of non-invasiveness of large blood vessels with catheters, as is necessary with the most widely used method of measuring cardiac output presently in use, namely the thermodilution method.

Most gas exchange methods for measuring the cardiac output which have been attempted suffer from the problem of "recirculation" which limits them to only intermittent determinations of $\dot{Q}_c$ separated by relatively long intervals to wash out gas introduced by the previous determination. This restriction of frequency of taking readings of $\dot{Q}_c$ is necessary to ensure that $P_{\bar{v}gas}$ has returned to a value close to zero before another determination is performed. The same constraint also applies to methods using reactive gases. The term "recirculation" refers to the return back to the lungs in the mixed venous blood of gas that has previously been taken away from the lungs in the arterial blood.

It is an object of the present invention to overcome or at least alleviate one or more of the abovementioned difficulties of the prior art, or at least to provide the public with a useful choice.

SUMMARY

Accordingly in a first aspect the present invention provides a method for measuring the pulmonary bloodflow in a subject including:

isolating two or more divisions of the respiratory system, said divisions comprising the complete gas exchanging part of said respiratory system, ventilating each said division with a separate gas mixture, at least one of said gas mixtures including an inert soluble gas, determining uptake of inert soluble gas in at least two of said divisions, determining uptake of oxygen in each of said divisions, determining end tidal concentration of inert soluble gas in at least two of said divisions, and calculating pulmonary bloodflow from determined values of uptake and end tidal concentration of inert soluble gas, and uptake of oxygen.

Preferably two or three divisions of the respiratory system are isolated, most preferably three divisions.

When three divisions are isolated it is preferred that two of the divisions are ventilated with gas mixtures which are substantially balanced with respect to inert soluble gas, the concentration of inert soluble gas in each of these two divisions being different from each other, and the third division is ventilated with a gas mixture which is unbalanced with respect to inert soluble gas.

One method of isolating two or more divisions of the respiratory system utilises a multi-lumen cuffed endobronchial catheter.

Accordingly in a second aspect of the invention there is provided apparatus for measuring pulmonary bloodflow in a subject including:

a multi-lumen cuffed endobronchial catheter adapted to allow separate gas mixtures to be provided to two or more separate divisions of the respiratory system of the subject, said separate divisions comprising the complete gas exchanging part of said respiratory system, two or more breathing systems for supplying different mixtures to each lumen of said multi-lumen catheter at the same rate and the same total pressure, two or more gas delivery systems for providing gas mixtures to said two or more breathing systems, sampling means for sampling (i) inspired and expired gas in each division and/or (ii) the fresh flow gas and the exhaust gas of each division, and gas analyser for determining concentrations of gases in said samples, a flow determining means for determining flow rates of (i) said inspired and expired gas and/or (ii) said fresh flow gas and exhaust gas and, processing system for calculating pulmonary blood flow from said determined concentrations and flow rates.

One method of ensuring that the gas mixtures are supplied to each lumen at the same rate and the same total pressure is to use a bag-in-a-box type ventilator with each breathing system, and operate the ventilator by supplying a common working gas. Other methods for synchronising the rate and pressure of mixed gas supplied to the lumens of the catheter would be evident to a person skilled in the art.

It is to be noted that the defined apparatus is not essential for use of the method of measurement defined above, but represents a particularly convenient apparatus useful in making the required measurements.

Endobronchial catheters having more than two lumens are novel and represent a third aspect of the present invention. Particularly accurate results can be obtained if the multi-lumen cuffed endobronchial catheter has three lumens.

Accordingly in a fourth aspect of the invention there is provided a triple lumen, cuffed endobronchial catheter for providing separate gas mixtures to each of three separate divisions of the respiratory system of a subject, said three divisions comprising the complete gas exchanging part of said respiratory system, said catheter comprising:

a primary tube having three lumens adapted to be inserted within the trachea of a subject, each of said lumens opening at a top end thereof into a connector tube adapted to be connected to a breathing system, and opening at a bottom end thereof into an outlet for delivering a gas mixture to one of said divisions, one or more inflatable cuffs located about said primary tube and/or said outlets adapted to form seals within the respiratory system such that each outlet is capable of delivering a gas mixture to one of said three separate divisions in isolation from each of the other divisions.

The outlet may be an opening in a tube, or a short tube with an opening, for delivering a gas mixture to a division of the respiratory system from a lumen of the primary tube. The outlet may be an extension of a lumen of the primary tube or may be an opening in the bottom end of a lumen.

The triple lumen cuffed endobronchial catheter preferably has an inflatable cuff located about the primary tube and above the outlets which is adapted to form a seal within the trachea.

In a particularly preferred embodiment the triple lumen catheter includes a first inflatable cuff as described above in combination with a second inflatable cuff located between the first and third outlets for forming a second seal in the right bronchus and a third seal in the hyparterial bronchus, the third seal allowing the third outlet to provide a gas mixture to the middle and lower lobes of the right lung and the second and third seals together allowing the second outlet to provide a gas mixture to the upper lobe of the right lung.

The second inflatable cuff preferably encircles the second outlet and lies within the right main bronchus and the hyparterial bronchus.

It is also possible to manufacture triple lumen catheters with inflatable cuffs as described above which are adapted to supply gas mixtures to the right lung, the upper lobe of the left lung and the lower lobe of the left lung, although for technical reasons it is less convenient.

DETAILED DESCRIPTION OF THE INVENTION

According to the present invention the measurement of pulmonary blood flow or cardiac output can be made at short intervals for an extended period of time, while avoiding the problems of recirculation. The measurements can be made rapidly and the calculations may be performed using appropriate software on a computer.

Anaesthesia is normally given through a single anaesthetic breathing system, however the present invention involves the use of more than one breathing system. Satisfactory results are obtainable with two breathing systems, however more accurate results can be obtained with three. Further improvement is theoretically possible with more than three breathing systems.

Each breathing system delivers to the subject its own individual adjustable ventilating gas mixture to one division of the subject's alveolar volume through its particular branch of the bronchial tree.

Such a set-up ensures that every part of the total alveolar gas volume (i.e. the complete gas exchanging part of the respiratory system) was being ventilated through one or other of the airway divisions, but no part was being ventilated through more than one airway division. The number of such divisions which is possible is only limited by technical considerations.

The simplest example of such an arrangement, readily achievable with existing anaesthetic equipment, has two such divisions, namely the left lung and the right lung.

After placement of a conventional endobronchial double-cuffed, double-lumen catheter (a "double lumen tube"—e.g. Bronchocath or Robertshaw type) the left lung and the right lung may each be ventilated with entirely separate gas mixtures administered through entirely separate breathing systems each served by its own separate fresh gas supply by a dedicated gas delivery system. Alternatively a custom made double lumen tube which ventilates (1) the right upper lung lobe and (2) the remainder of the respiratory system could readily be designed along the lines of previously mentioned triple lumen tube but with combined first and third lumens.

The subject on whom this method is being used to determine the cardiac output might be, by way of example, a patient undergoing general anaesthesia and the inert gas might be nitrous oxide ($N_2O$). In this case $N_2O$, being an anaesthetic drug, is contributing to the patient's anaesthetic state, but this need not necessarily be so for other inert gases.

In this case the total alveolar volume is divided into two divisions, namely the left lung and the right lung and the airway is likewise divided into two divisions, one for each lung.

Each lung is then ventilated with a gas mixture supplied to it by its own breathing system. Any workable breathing system would suffice. In a typical arrangement used for general anaesthesia there would be inflow into the breathing system of component gases under the control of the anaesthetist by a needle valve for each. In this case two of the components would be $O_2$ (used in all cases) and $N_2O$. The anaesthetist generally observes the flow rate of each gas flow he controls by means of a gas rotameter or other continuously measuring flowmeter.

The breathing systems may contain fresh canisters of soda-lime to absorb the $CO_2$ produced by the patient, for example semi-closed or closed circle absorber systems (SCCA or CCA). Alternatively they may not contain soda-lime, e.g. Mapleson systems A to E. A preferred type is the Humphrey ADE low-flow multipurpose breathing system, adaptable to both soda-lime absorption or to Mapleson A or Mapleson D systems without soda-lime. (An advantage of this make is a low circuit volume made possible by its flexible-tube design. It can also be readily converted from spontaneous breathing mode to IPPV mode by flicking a switch.)

The most preferred type is the non-rebreathing system whereby the fresh gas flow from the gas delivery system is also the inspiratory gas and the expiratory gas is the same as the exhaust gas.

Except in a completely closed system every breathing system possesses a spill-valve to vent excess gas, i.e. exhaust gas, from the circuit either under manual control or acting automatically.

Each breathing system may connect to the external opening of one of the lumens of the multi-lumen endobronchial catheter, usually via a connector tube, which may include a catheter mount. Breathing system gas passes into the patient with each inspiration, and expired gas the other way during expiration.

The preferred form of the invention employs three breathing systems and three divisions of the respiratory system.

One method of doing this entails the use of a small diameter cuffed flexible catheter passed down one or other lumen of the double lumen tube. It is pushed down into the lung until it will go no further and the cuff inflated with a minimum volume of air or fluid. The top end comes out near the top end of the larger tube through an opening in its side, ensuring there are no leaks from the larger tube at the point of exit. The small tube ventilates a segment of one lung and the larger tube the remainder of that lung. The other lumen of the double lumen tube functions as described in relation to the double lumen system described above.

A similar procedure can be carried out with two such small catheters passed through a cuffed endotracheal tube.

The small diameter cuffed flexible catheter may be, for example, a Foley's urinary catheter or a Swan-Ganz catheter or similar or custom-made type.

The preferred form of subdividing ventilation of the alveolar volume into three divisions consists of a custom-made preformed triple-lumen catheter analogous in structure to a double lumen tube. This is termed a "triple lumen tube" or "triple lumen catheter".

A triple lumen tube is preferred to the three-division methods described above because its position in the patient's bronchial tree can be checked by fibreoptic bronchoscopy whereas a cuffed flexible catheter is placed blindly and is also prone to migration after placement because of its flexibility. This may result in occlusion of tie opening of a bronchus that branches off the lumen of the bronchus in which the inflated cuff of the catheter lies. This will cause collapse of a segment of a lung. Though this may happen without serious immediate effects, in the presence of lung pathology it could possibly cause e.g. local infection or other local pathology in the longer term.

The following parameters may be monitored using techniques known to the art, e.g. using appropriate gas sampling and analysing equipment.

(i) The uptake or excretion of one or more of the gas species by the subject, from the fresh gas flow, "FGFgas", between its point of entry into the system and its point of exit from the system in t he exhaust gas flow, "EXHgas".

(ii) The end-tidal concentrations of one or more of the inert soluble gases present.

In a preferred embodiment the uptake or excretion of each separate gas species from each breath is measured at the external end of the divisional lumen of the endobronchial tube. The term "breath" as used herein refers to one respiratory cycle. The term "uptake" as used herein refers to both uptake and excretion, excretion being a negative value of uptake.

This latter measurement considerably improves the response time of the cardiac output measurement, i.e. its responsiveness to transient or rapid changes of the cardiac output, but the cardiac output could still be measured, though with a slower response time if this latter measurement were omitted.

The arrangement described below follows the usual anaesthetic equipment pattern:

Each divisional alveolar volume may be served, from above downward, by a gas delivery system, consisting of separate sources of gas flow, one for each type of gas, each with a flow control and, for safety reasons, a visual monitor of the instantaneous flowrate of each of the separate gas flows. These gas flows are joined together in a single mixed flow and pass to a breathing system. The breathing system allows the inspiratory gas mixture to enter and leave the divisional alveolar volume either by normal breathing action, or (preferred) by the action of a ventilator. The exhaust gas leaves the breathing system at some point in it. The preferred point of exit is from the ventilator reservoir bag (concertina bag) in the case of the bag-in-a-box type ventilator.

Gas in the breathing system enters one lumen of a multi-lumen tube, there being one lumen for each gas delivery system/breathing system combination, and enters the divisional alveolar volume during inspiration. It leaves again during expiration. As it enters and exits the tube lumen the gas may be sampled and analysed at a continuous small rate. Where a separate flow measuring device is in use for measuring body uptakes, it is also preferably located here. For whole system uptakes, sampling for gas analysis and separate flow measurement devices may be at two locations—(1) in the gas delivery system, between the union of flows of separate gas flows and the common gas outlet and/or (2) in the tube leading away exhaust gas.

Whether uptakes are being measured between divisional FGFgas and EXHgas (whole system uptakes) or between the divisional inspiratory flow and expiratory flow of every breath (body uptakes) there is a range of ways by which these uptake measurements can be made.

The advantage of measuring body uptakes over whole system uptakes is that the response time is faster because the only volume buffering change is the divisional respiratory system volume. In the case of whole system uptakes the volume buffer also includes the volume of the divisional breathing system.

The advantage of measuring whole system uptakes is that they are more easily performed because thorough mixing of the gas flows can be more easily secured and therefore greater accuracy is achieved.

As there is a trade-off between the advantages, the preferred arrangement is to measure whole system uptakes and body uptakes in combination. This allows an optimum resultant accuracy and response.

Examples of methods for measuring the necessary uptakes are given below. Each of these methods may be applied to either whole system uptakes or body uptakes, and either in whole or in part. The ter "inflow" applies either to divisional FGFgas or to divisional inspiratory flow in this section according to context, and similarly "outflow" applies to EXHgas or to divisional expiratory flow.

The Use of Flow Measuring Devices

Examples of flow measuring devices include the pneumotachograph, the hot wire anemometer and the turbine anemometer. Other devices which measure gas flow accurately are also suitable.

The response time of the flow measuring device is relevant if the flow of gas changes over time. The response time is preferably such that the device is capable of following flow changes closely. Iycompatibnc response times will result in even longer uptak. measurement times in the case of whole system uptakes. Contamination will occur between inspiratory and expiratory measurements in the case of body uptakes rendering them useless unless special breathing circuitry is employed.

In this regard inspiratory and expiratory sampling lines may be connected between the inspiratory and expiratory limbs respectively of an IPPV breathing system and a gas analyser. Sampling and analysis of the gas mixtures could be coordinated with the ventilator such that sampling and analysis of the inspired gas is triggered when the ventilator is in its inspiratory phase and vice versa. This could be achieved by an appropriate combination of solenoid valves on the sampling lines which are operated by a solenoid control unit which is coordinated with the ventilator operation.

Where the instrument response time is compatible with flow changes, the rapid response of the flow measuring device may be used in conjunction with a rapid gas analyser (RGA) to yield flowrate signals of individual gas species ($\dot{V}_x$).

For example a digitized signal stream from an RGA sampling the gas mixture can represent individual values of $F_x$ (the fractional concentration in the gas mixture of gas x). This stream may be combined with a corresponding stream of $\dot{V}_I$ or $\dot{V}_E$ signals representing instantaneous inspiration or expiration signals respectively from such a flow measuring device such that each signal from the RGA corresponds in time with a signal from the device. By a computational process the $F_x$ signals from the RGA may be multiplied by the corresponding $\dot{V}_I$ or $\dot{V}_E$ signals from the device to form a resultant stream of signals, each representing the instantaneous flowrate of x into or out of the subject's divisional airway and alveolar volume, $\dot{V}_{Ix}$ or $\dot{V}_{Ex}$. Integration of this resultant stream of signals over the time interval of measurement, t, gives the volume of x that has passed over this time $V_{TIx}$ or $V_{TEx}$.

The time interval chosen is conveniently the duration of inspiration or the duration of expiration in the case of body uptakes, the instrument detecting tie changeover moment from inspiration to expiration as the moment of zero flow separating positive (inward) values of flow from negative (outward) ones.

If the inward passing and outward passing volumes of x are thus measured with each breath then the difference between them is the uptake with each breath, $U_{Tx}$. The rate of uptake of x, $\dot{U}_x$, is $U_{Tx}$ multiplied by the respiratory rate, RR. Alternatively $\dot{U}_x$ may be determined more directly by taking the average of ($\dot{V}_{Ix}$-$\dot{V}_{Ex}$) evaluated over an integral number of respiratory cycles. Algebraically:

$$\dot{V}_{Ix} = F_x \cdot \dot{V}_I \quad \text{and} \quad \dot{V}_{Ex} = F_x \cdot \dot{V}_E$$

$$V_{TIx} = \int_o^t \dot{V}_{Ix} \quad \text{and} \quad V_{TEx} = \int_o^t \dot{V}_{Ex}$$

$$U_{Tx} = V_{TIx} - V_{TEx}$$

$$\dot{U}_x = U_{Tx} \cdot RR$$

The Use of An Insoluble Gas to Measure Flow

An insoluble gas, "marker gas", can be added at a steady known flowrate, $\dot{V}_{marker}$, to an inflow, is allowed to mix radially and is then sampled periodically by a gas analyser. The total flow rate of gas, $\dot{V}_I$, is:

$$\dot{V}_I = \dot{V}_{marker}/F_{Imarker}$$

where $F_{Imarker}$ is the fractional concentration of marker gas measured.

If the sampling rate and the analyser's response time are sufficiently fast the $\dot{V}_I$ signals may be used inexactly the same way as the $\dot{V}_I$ signals generated by a flow measuring device and uptakes of any gas of interest may be measured on a breath to breath basis.

To achieve this end, expiratory flows are most conveniently measured by using a second marker gas (another species of insoluble gas). In one arrangement a single sampling point not far beyond the external end of the divisional lumen of the multi-lumen tube may be flanked by two marker gas delivery ports to the airway, one on each side. The distance between each port and the sampling point is sufficient to allow radial mixing of marker gas in the gasflow.

Marker gases may be any non-toxic insoluble gas. Examples of such a gas include helium, nitrogen, argon, sulphur hexafluoride, neon and many others. It may be used in any convenient concentration taking into account body tissue stores in the case of a gas found naturally in the atmosphere. This applies particularly to nitrogen but if trace concentrations are to be used it may apply to other gases as well.

Volume Displacement Devices $V_{TI}$ may be measured this way. A piston pump is an example when used as a ventilator when due correction is made for compliance within the breathing system. Another more common example is the concertina bag of a bag-in-a-box ventilator where the volume of gas delivered by the bag can be regulated by a mechanical stop inside the box. $V_{TE}$ may also be measured by volume displacement whereby a spirometer for example may be used, or the concertina bag may be caused to function like a spirometer. Spontaneously breathing patients may breathe into and out of a spirometer. In all these cases, spirometer or bag displacement may be transduced into an electrical signal for the purposes of further calculations.

Mixing Devices $F_{marker}$ and $F_x$ measurements may be considerably simplified if discrete volumes of gas are mixed longitudinally before measurement because then complex mathematical processes and fast response times can be dispensed with.

Mixing may be performed by passing the flows of gas through mixing boxes, or by stirring them by e.g. a fan, or employing other similar means of either mechanical baffles or active mixing.

Constraining to Uniform Flowrate

If inspiration and expiration occur at a constant flowrate and a sufficiently large number of gas analyses are made during the course of a single breath, simple inspiratory or expiratory averaging of multiple values for $F_{marker}$ and $F_x$ simplifies the calculation of mass transfer because unit time in this case is exactly equivalent to unit volume.

Suggested Gas Analysis Techniques

Gas concentrations may be measured by any suitable technique but a form of rapid gas analysis may provide the best data by reason of (a) rapid response rate to change and (b) by averaging, giving a more precise determination. Suitable RGA devices include mass spectrometers, infrared spectrometers, photoacoustic devices, paramagnetic and paramagnetic acoustic devices and Raman scatter analysers.

Calculation of $\dot{Q}_c$

The ratios of $O_2$ uptakes of subdivisions of the total alveolar volume are assumed to accurately reflect their relative pulmonary blood flows. This will certainly be true if pulse oximetry shows a high haemoglobin $O_2$ saturation (e.g. 95%–100%). (Pulse oximetry is universally used as a monitoring modality for severely ill and anaesthetised patients.) If the haemoglobin $O_2$ saturation is not high the ratios represent flows of oxygenated blood through the subdivisions.

From the foregoing measurements and the end-tidal $F_{AN_2O}$ values, $\dot{Q}_c$ can be calculated as follows.

The calculations will be illustrated by reference to the two division model previously outlined but corresponding equations exist to apply to any number of divisions. For the purpose of the following mathematical discussion $N_2O$ will be used as the type gas but any soluble inert gas "x" will also give a valid result.

The uptakes of $N_2O$ ($\dot{U}_{N_2OL}$ and $\dot{U}_{N_2OR}$) for the left and right lungs respectively are governed by their respective alveolar fractional partial pressures of $N_2O$ ($F_{AN_2OL}$ and $F_{AN_2OR}$), the mixed venous fractional pressure of $N_2O$ ($F_{\bar{v}N_2O}$), the Ostwald solubility coefficient for $N_2O$, $\lambda$, and the respective lung shares of the cardiac output ($\dot{Q}_{cL}$ and $\dot{Q}_{cR}$)

$$\dot{U}_{N_2OL} = \dot{Q}_{cL}\lambda(F_{AN_2OL} - F_{\bar{v}N_2O}) \qquad 1$$

$$\dot{U}_{N_2OR} = \dot{Q}_{cR}\lambda(F_{AN_2OR} - F_{\bar{v}N_2O}) \qquad 2$$

The respective uptakes in the left and right lungs are measured simultaneously so that $F_{\bar{v}N_2O}$ is the same in each.

The most effective values to use for $F_{AN_2OR}$ and $F_{AN_2OL}$ are when the two values are as widely separated from each other as possible, in order to maximise $N_2O$ transfer in the lungs and thereby make $N_2O$ uptake measurements more precise. Preferably one lung is ventilated with a gas mixture containing 60% to 80% of $N_2O$ (soluble inert gas) while the other lung is ventilated with a gas mixture containing 0–20% $N_2O$, preferably 0%. More preferably one lung is ventilated with a gas mixture containing $$\frac{Bp(\text{mmHg}) - 150}{Bp(\text{mmHg})} \times 100\% N_2O$$

while the other lung is ventilated with a gas mixture containing no $N_2O$.

Preferably there is positive uptake in one lung and negative uptake (excretion) in the other lung.

The ratio of the respective oxygen uptakes, $\dot{U}_{O_2R}$ and $\dot{U}_{O_2L}$, equals the $\dot{Q}_{cR}$ to $\dot{Q}_{cL}$ ratio:

$$\dot{Q}_{cR}/\dot{Q}_{cL} = \dot{U}_{O_2R}/\dot{U}_{O_2L} \qquad 3$$

This can be shown as follows:

Under anaesthesia there could be areas of the lung that are poorly ventilated so that the haemoglobin of the blood passing through such an area is less than 100% saturated with oxygen when it passes on into the arterial system.

The "$SpO_2$" measures the saturation in the arterial system and is a universal monitor. If the $SpO_2$ indicates that the haemoglobin is saturated ($SPO_2 \approx 100\%$) this indicates there are no poorly ventilated areas. If this is the case (which is usual) the uptake of oxygen from any given area of the lung, or from the right lung to the left lung is strictly proportional to the blood flow through that area of lung.

This statement is not true for the uptake of $N_2O$ or any other gas that does not saturate a carrier molecule such as haemoglobin. In these cases less $N_2O$ is taken up by poorly ventilated areas than by well ventilated ones even if the respective blood flows are equal, because $N_2O$ obeys Henry's Law and less of it dissolves in blood when there is less in the alveolar gas, more of it when better regional ventilation produces more in the alveolar gas of that region.

To summarize when $O_2$ fully saturates its carrier molecule haemoglobin, its concentration in blood is always the same. All mixed venous blood returning to the heart from the rest of the body has the same level of desaturation at a particular moment in time (usually about 75%). Therefore the uptake of $O_2$ from particular places in the lung must depend on the blood flow rate to that place and only on this whereas for $N_2O$, which obeys Henry's Law, uptake will depend both on the regional blood flow rate and on the regional concentration of $N_2O$ in the regional alveolar gas.

Therefore equations 1, 2 and 3 above are simultaneous and contain three unknowns, namely $\dot{Q}_{cR}$, $\dot{Q}_{cL}$ and $F_{\bar{v}N_2O}$. Now:

$$\dot{Q}_c = \dot{Q}_{cL} + \dot{Q}_{cR}$$

The calculations can be carried out on line by a computer.

The above set of simultaneous equations, lead when solved to the following equation:

$$\dot{Q}_c = \frac{\dot{U}_{N_2OL}\left(1 + \frac{\dot{U}_{O_2R}}{\dot{U}_{O_2L}}\right) - \dot{U}_{N_2OR}\left(1 + \frac{\dot{U}_{O_2L}}{\dot{U}_{O_2R}}\right)}{\lambda(F_{AN_2OL} - F_{AN_2OR})} \qquad 4$$

The assertion above that the most effective values for $F_{AN_2OR}$ and $F_{AN_2OL}$ are when the two values are as widely separated from each other as possible can be demonstrated with the help of this equation. The values of $F_{AN_2OL}$ and $F_{AN_2OR}$ being as widely separated is achieved when $F_{IN_2OL}$ and $F_{IN_2OR}$ will be as widely separated as possible also, $F_{IN_2OL}$ and $F_{IN_2OR}$ being the inspired fractional $N_2O$ concentration in the left and right lungs respectively. ($F_{AN_2OL}$ and $F_{AN_2OR}$ are measured by the RGA as the concentration of $N_2O$ in the expired gas at the end of expiration.)

As these two values become less widely separated the quantity ($F_{AN_2OL} - F_{AN_2OR}$) becomes smaller. As this is the difference between two measured quantities the relative error of this difference becomes greater and greater, tending toward infinity as ($F_{AN_2OL} - F_{AN_2OR}$) tends towards its lower limit of zero. Therefore the error of $\dot{Q}_c$ also approaches infinity as the end expiratory concentrations of $N_2O$ become equal to each other in the two divisional alveolar volumes (which in this case are the left lung and the right lung).

More than one soluble inert gas may be used in the gas mixture. In this case it is possible to calculate the cardiac output by the two separate sets of results and then combine the measured cardiac output of each inert gas calculation into a single value by weighting each according to its estimated margin of error in the appropriate manner. These calculations are preferably carried out by a computer.

The double lumen endobronchial cuffed tube may be modified into a triple lumen tube. The third lumen may serve the right upper lobe bronchus or the left upper lobe bronchus.

One advantage of a third lumen is that it may be ventilated with air or a gas mixture containing insoluble gas. The inflow of fresh gas to a closed circle breathing system without soda-lime that is connected to the third lumen (third division of the respiratory system), could be cut off for prolonged periods because uptake from it would be very slow because of the presence of insoluble gas. (Any gas removed from this system through sampling needs to be replaced with insoluble gas or air.) The mixed venous partial pressure of each gas dissolved in mixed venous blood would rapidly come into equilibrium with the gas in the rebreathing system of the third lumen, from which soda-lime is omitted so $CO_2$ is also in equilibrium. In this way the mixed venous tensions of all relevant gases, which would be of interest and value to the anaesthetist in their own right, could be given to him. This can be done by ventilating the division and sampling of end-tidal gas. In addition a direct knowledge of the partial pressure fraction of the soluble inert gas in the mixed venous blood would increase the accuracy of the $\dot{Q}_c$ determination when compared with the independent determination calculated as in the foregoing equations, and used to correct it.

A further advantage of a third lumen is that it can reduce errors associated with a phenomenon called $\dot{V}/\dot{Q}$ mismatch.

A theoretical assessment of the error associated with the pulmonary bloodflow measurement indicates that the major source of error is likely to reside in $\dot{V}/\dot{Q}$ mismatch.

This is an imperfection in lung physiology which essentially implies a failure to match the ventilation of every portion of the lung exactly to its perfusion with blood.

The term "perfusion" refers to the flowrate of blood through unit volume of lung. Normally the lung is perfused with blood rather unevenly such that the most dependent parts of the lung, i.e. the lower parts, have a higher perfusion than those not so dependent. A change in body position means that any particular small region of the lung will probably change its perfusion by reason of changing its vertical distance from the heart, which is the controlling factor. The distribution of blood flow throughout the lungs will change.

Along with this there is also a change in the regional distribution of ventilation which quite closely matches the change in blood flow. Normally all parts of the lung have a ratio of ventilation to blood flow, the $\dot{V}/\dot{Q}$ ratio, that is approximately the same, and normally about 0.8 at rest. This value of 0.8 is likely to change, with exercise for example, but its uniformity changes much less, ventilation is matched by the body to perfusion.

If $\dot{V}/\dot{Q}$ matching is perfect it can be shown mathematically that the partial pressure of all gases of interest in the end expired breath (excluding the dead space, namely the bronchial tree, within which there is no gas exchange) is equal to the partial pressure of those gases in the arterial blood. Moreover these partial pressures are the same in all parts of the lung.

$\dot{V}/\dot{Q}$ matching is quite close to perfect in healthy young adult lungs. In childhood and in later life it is less perfect.

In all people it is not perfect under anaesthesia. Also in various forms of disease and even in such body states as obesity it is likely to worsen. Thus in all human patients under anaesthesia $\dot{V}/\dot{Q}$ mismatch will be encountered, and when anaesthesia is combined with age factors, body weight, and body position (lying flat is worse in this respect than sitting or standing) and the effect on the lungs of e.g. smoking, quite considerable degrees of it can be encountered.

It can be shown mathematically that in the presence of $\dot{V}/\dot{Q}$ mismatch the partial pressure of a gas in the end-expired breath (excluding dead space gas, namely the first part of the expired breath) will no longer be equal to its partial pressure in the arterial blood. It is reasonably close but it is no longer exactly the same.

Prior art has accepted the errors inherent in this and a number of published papers show reasonable agreement between the cardiac outputs measured by prior art gas uptake methods of measuring the cardiac output and alternative methods of measuring it they have been tested against. The present method is expected to be capable of demonstrating reasonable agreement with existing methods that do not rely on gas exchange (thermodilution being the most widely used of these). A study in older and sicker patients where appreciable $\dot{V}/\dot{Q}$ mismatch is expected has confirmed this.

However apart from technical errors $\dot{V}/\dot{Q}$ mismatch remains a source of error that is unquantified. It is believed that this problem may be overcome using one of the possible methods that a triple lumen tube makes possible.

While not wishing to be limited to theory it is believed that the invention will give more reliable results if three alveolar volume divisions are used on the basis of a technique which can overcome the problem of $\dot{V}/\dot{Q}$ mismatch.

Theoretical Source of Error

1. $\dot{V}/\dot{Q}$ mismatch is a phenomenon exhibited by all functioning lungs. If we consider a young adult lying in the supine position there is a small discrepancy between the $F_{N_2O}$, in the case of $N_2O$ (as a soluble inert gas), as measured by a gas analyser in a gas sample taken from the end of expiration, $F_{AN_2O}$, and the $F_{N_2O}$ of the blood that is draining the lungs, $F_{aN_2O}$. In this example the subject is breathing a gas mixture of uniform composition into both lungs. The $F_{N_2O}$ (of blood) can only be accurately measured by specialized techniques. The discrepancy is evaluated as A-a$DN_2O$.

If this discrepancy is sufficiently large it will interfere with the accuracy of the measurement of $\dot{Q}_c$ because the equation where $\dot{Q}_c$ is derived contains the variables $F_{AN_2OL}$ and $F_{AN_2OR}$. The variables which are readily measurable are taken to be equal to the equivalent variables in blood, $F_{aN_2OL}$ and $F_{aN_2OR}$ and the equation referred to should be properly written with $F_{aN_2OL}$ and $F_{aN_2OR}$ in the place of $F_{AN_2OL}$ and $F_{AN_2OR}$. It would be entirely impractical to measure the variables $F_{aN_2OR}$ and $F_{aN_2OL}$ directly as this would involve sampling blood from the pulmonary veins, deep inside the chest.

However this source of error can be entirely eliminated if all alveoli-in a single alveolar division can be caused to have exactly the same concentration of gases in them. The usual situation is that there is a spread of concentrations of $F_{N_2O}$ within a division because there is a spread of $\dot{V}/\dot{Q}$ ratios within the division. The term $\dot{V}/\dot{Q}$ means the ratio of ventilation, $\dot{V}$, that a particular alveolus gets to its perfusion, $\dot{Q}$. The value of $F_{AN_2O}$ found within its contained gas mixture will be different from that found within another alveolus if the $\dot{V}/\dot{Q}$ is different.

2. Theory of balanced uptake

If however the component gases of the inspired gas mixture, in particular the most abundant ones, $N_2O$ and $O_2$, are entering the blood at the same relative rate that they are being delivered to the alveolus from above, the rate at which these two gases are taken up by the blood becomes dependent only on the blood flow. The ventilation becomes irrelevant because in this case (and only in this case) the inspired gas mixture, the alveolar gas mixture, and the expired gas mixture become identical in composition. This state is described here as balanced uptake.

It can be described mathematically and it is found that for normal adult values of $\dot{Q}_c$ and whole body $\dot{U}_{O_2}$, and $F\bar{v}_{N_2O}$, may not be more than approximately 0.37 in value.

At this value of $F\bar{v}_{N_2O}$ there is one possible gas mixture that can be given to the subject that will produce balanced uptake. Below this value of $F\bar{v}_{N_2O}$ and right down to a zero value of $F\bar{v}_{N_2O}$ there are always two possible inspired gas mixtures Of $O_2$ and $N_2O$ that can be given to the subject that will result in balanced uptake occurring. At $P\bar{V}_{N_2O}=0$ for example the two gas mixtures are 0% $N_2O$ and about 80% $N_2O$. As the $P\bar{V}_{N_2O}$ rises toward 0.37 the value of $F_{IN_2O}$ (the inspired $N_2O$ level) rises from zero in one mixture while it falls from 80% in the other, becoming the same at $FV_{N_2O}=0.37$ where it comes to lie between 60 and 70%.

For complete balanced uptake, carbon dioxide ($CO_2$) also must be added to the inspired gas mixture in physiological concentration.

It has now been discovered that the composition of the right breathing mixture, the "balanced-uptake" mixture, can be calculated from a knowledge of both the cardiac output and the mixed venous fractional pressure of $N_2O$, $F\bar{v}_{N_2O}$ (and also the haemoglobin concentration).

It turns out that for $F\bar{v}_{N_2O}$ values in the range that will be present in most patients, for every specific value there are two possible gas compositions, that is to say two possible ratios of nitrous oxide to oxygen in the balanced uptake mixture. This being the case it is possible to find these ratios simultaneously by trial and error by using two lumens of a triple-lumen tube, one for each of the two balanced uptake mixtures. The third lumen would ventilate either a segment of a lung or an entire lung with a non-balanced mixture. The need for this arises because the value of $F\bar{v}_{N_2O}$ needs to be kept stable over time and under proper control.

Such a system ensures that the alveolar gas mixture in each compartment (whole lung or segment thereof) is uniform in composition throughout that compartment and that the perfusing blood that leaves the compartment (to mix with the blood leaving the other two compartments and form the arterial stream) has fractional pressure values of $N_2O$ that are the same as the $F_{N_2O}$ of the breathing gas mixture for the two balanced uptake mixture compartments.

Accordingly it is believed that this innovation would improve the precision and accuracy of the method very considerably.

The invention will now be described with reference to some examples and drawings which illustrate some preferred aspects of the present invention. However it is to be understood that the particularity of the accompanying examples and drawings is not to supersede the generality of the preceding description of the invention.

Figure 1:
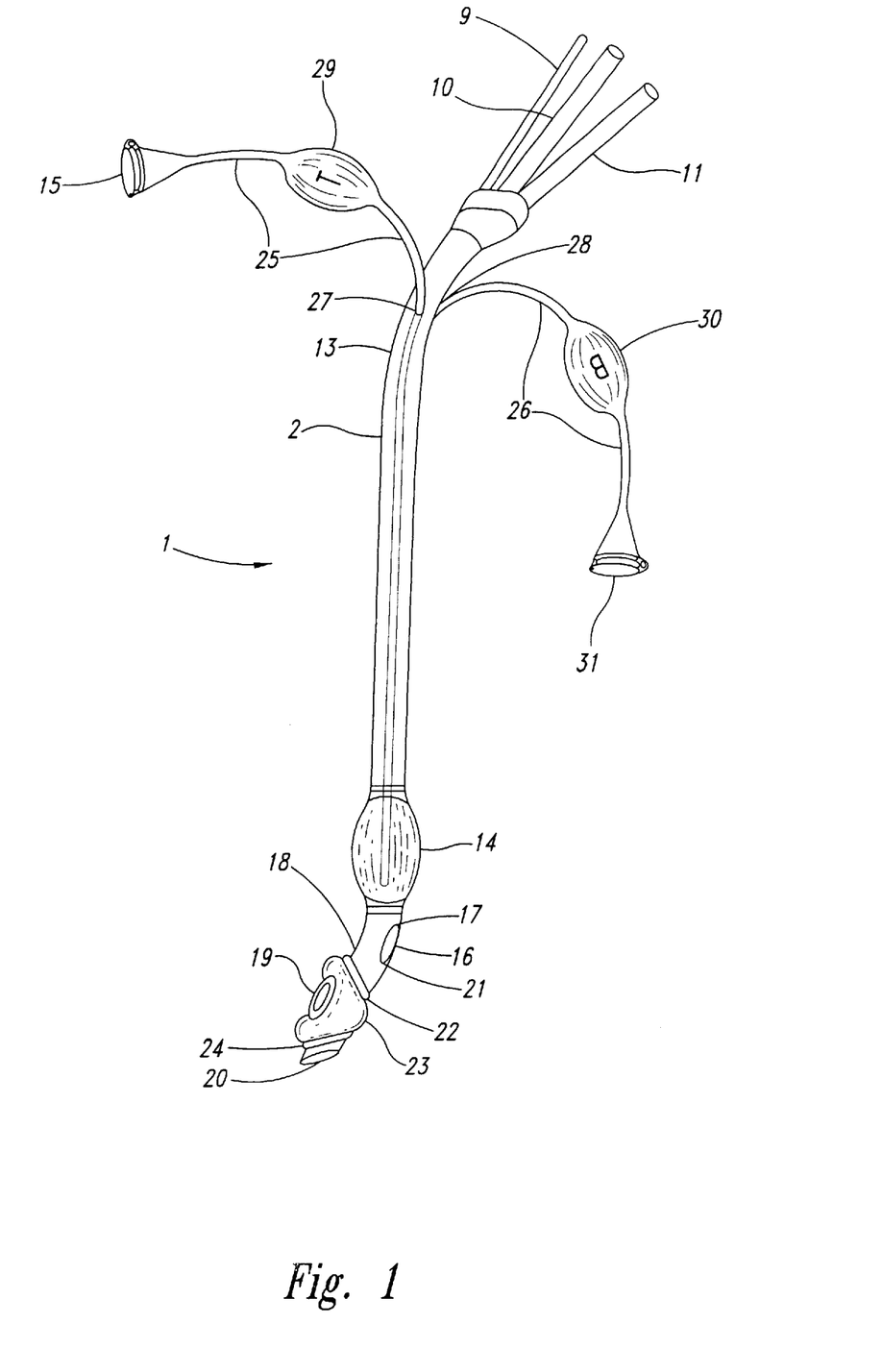
FIG. 1 is a perspective view of a triple lumen, cuffed endobronchial catheter according to the invention.

Referring to the drawings FIG. 1 shows a triple lumen cuffed endobronchial catheter 1 having a primary tube 2 which includes three lumens (not visible). The three lumens are for providing individual gas mixtures to the right upper lobe bronchus 3 feeding the upper lobe of the right lung 4, the right hyparterial (or right truncal) bronchus 5 feeding the middle and lower lobes of the right lung 6, and the left main bronchus (or left lung bronchus) 7 feeding the left lung 8, as showin in FIG. 2.

At the top of primary tube 2 the three lumens become three independent connector tubes 9, 10 and 11 which are located outside the mouth when the catheter is in position within the trachea 12 of a subject. Primary tube 2 is molded with a bend 13 towards the centre of its proximal half designed to overlie the tongue posteriorly down to the glottic opening.

Figure 2:
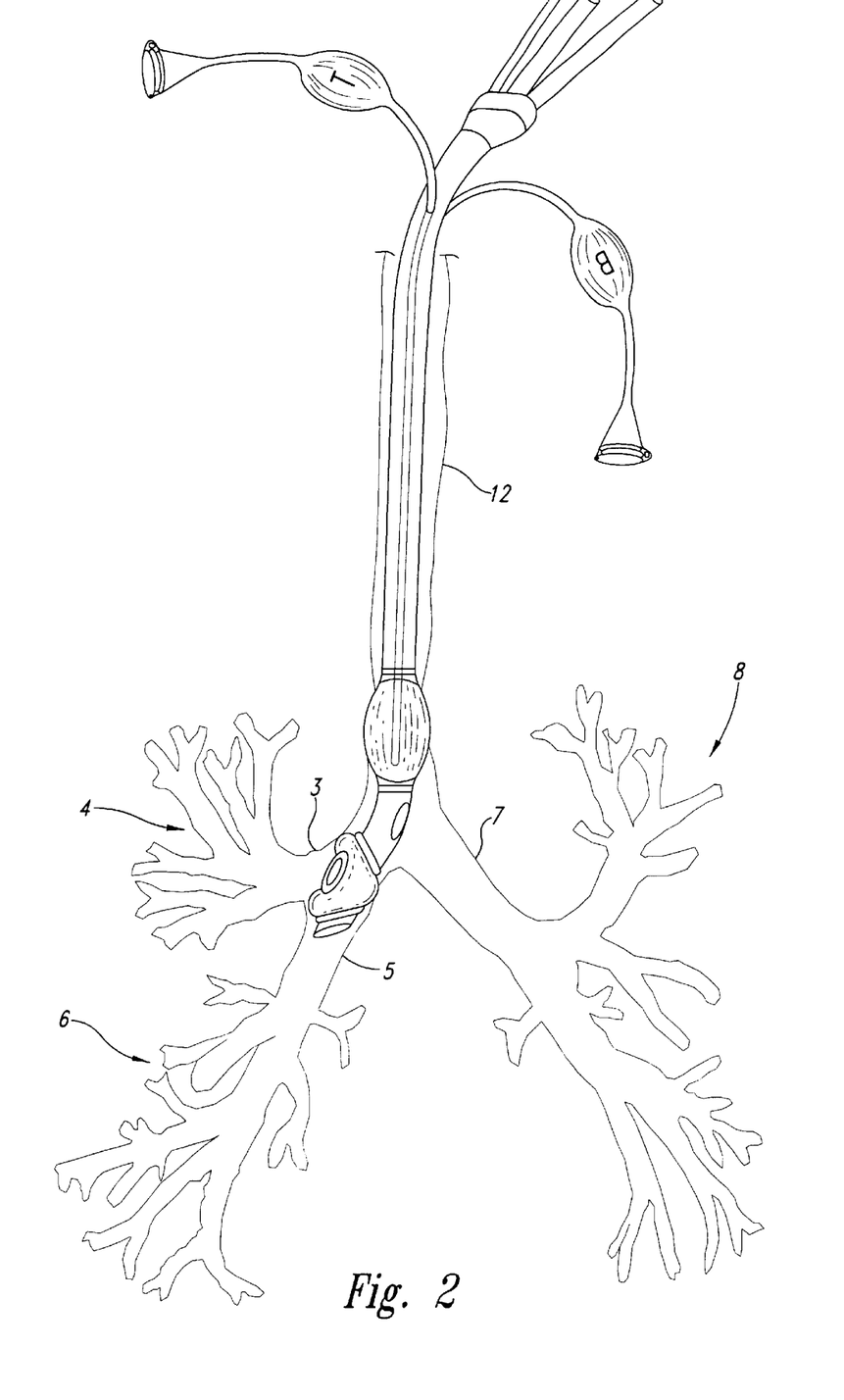
FIG. 2 is a partial cross sectional view of the triple lumen catheter of FIG. 1 inserted in the respiratory system of the subject.

Distally there is a tracheal cuff 14 which, when positioned, lies entirely within trachea 12 and when inflated through inflation funnel 15 firmly seals primary tube 2 within the trachea 12.

Immediately below the distal margin of the tracheal cuff 14 outlet 16 of one of the internal lumens opens to the exterior of the tube on its left hand side and terminates. This outlet 16 is at the bottom of the end of the lumen fed by connector tube 11 and provides gas mixture to the left lung 8. Its upper margin 17 lies about 2 cm distal to the tracheal cuff 14.

Beyond the outlet 16 a tube 18 containing outlets 19 and 20 curves to the right and slightly posteriorly. Outlets 19 and 20, which are in the form of two lumens or tubes, extend from the lumens of primary tube 2 to which connector tubes 9 and 10 respectively are associated.

Two centimetres below the lower margin 21 of outlet 16 and on the left side is the upper margin 22 of a distal inflatable cuff 23. This upper margin 22 then encircles tube 18 obliquely such that in oblique cross section along the line of the margin of the cuff the margin 22 extends proximally up the tube 18. On the tubes right side the margin is proximal to its level on the tubes left side by 1 cm.

The distal margin 24 of distal cuff 23 on the other hand obliquely crosses tube 18 in the other direction so that on the right side the margin 24 is distal by 1 cm and the width of the cuff 23 on the right side is much greater than its width on the left hand side—3 cm wide compared with 1 cm wide on the left.

When in position distal cuff 23 lies around the right main bronchus. The right hand part of the cuff 23 also extends into the hyparterial bronchus 5, which is the extension of the right main bronchus beyond the origin of the right upper lobe bronchus 3.

On the right hand side of the tube 18 and centered midway between the upper and lower margins of the distal cuff 23 outlet 19 opens to the exterior. Outlet 19 is elongated in the axis of the tube 18 and approximately 6–8 mm long by about 1½–4 mm wide. The distal cuff 23 surrounds opening 19 which opens into the upper lobe of the right lung 4. The distal cuff 23 is firmly attached to the outer surface of tube 18 to a distance 1–2 cm around the perimeter of opening 19.

One to two mm distal to the distal margin 24 of the distal cuff 23 tube 18 terminates at outlet 20. The cross-section at outlet 20 is oblique as it is parallel with the oblique distal marking of the cuff and outlet 20 is consequently oval in shape.

The tracheal cuff 14 and the distal cuff 23 are inflated by two cuff inflating tubes 25 and 26 respectively which open into them distally while proximally they extend within the body of primary tube 2 (as two small additional mini lumens) toward the proximal bifurcations 27 and 28 respectively. Beyond the bifurcations they extend 10 cm as independent tubes. Within this independent part of each tube 25 and 26 are pilot balloons 29 and 30 and at the proximal ends inflation funnels 15 and 31, which may be replaced by cuff valves mounted beyond female Luer connections.

The respective internal diameters of the three lumens should be 1:2:2 with the lumen feeding the right upper lobe being the smallest.

Figure 3:
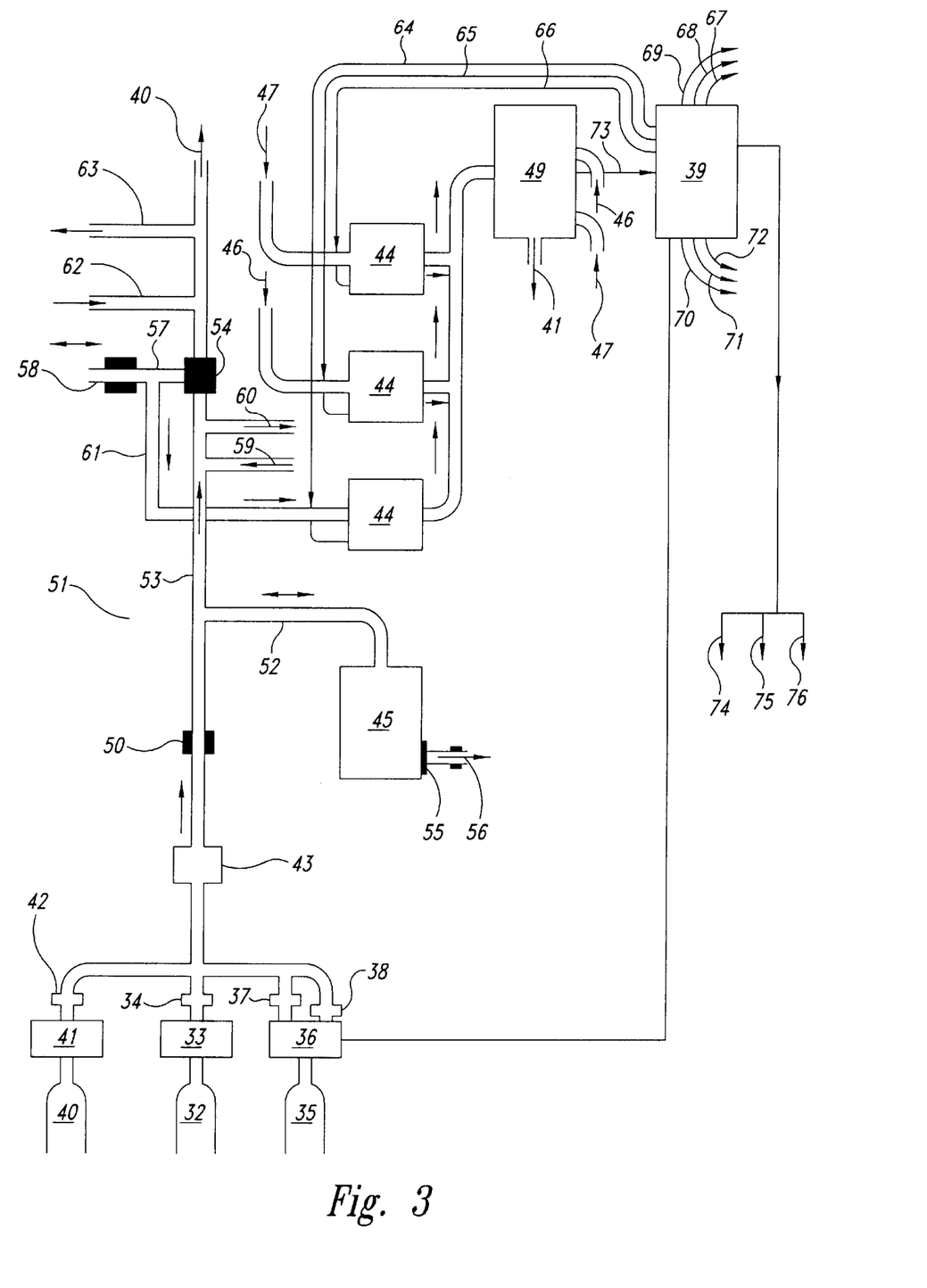
FIG. 3 is a diagrammatical representation of an apparatus useful for the measurement of pulmonary blood flow in a subject.

FIG. 3 is a diagrammatical representation of part of a preferred embodiment of the invention.

Notes:

1. Tubes carrying gas are denoted thus:=
2. Arrows alongside, or entering, or leaving denote direction of flows.
3. Ordinary arrows (→) denote one direction only and increasing flow.
4. Double ended arrows (÷) denote respiratory flow i.e. tidal in nature, with or without pauses of no flow, associated with inflation and deflation of a division of the respiratory system.
5. Electrical connections are denoted by single black lines. The direction of current is denoted by arrowheads on these lines (—).

A gas source of $O_2$ under high pressure 32 which may be contained for example in a cylinder, passes gas through a gas regulator or reducing valve 33 into a conducting pipe where it is of some lower pressure, 400 kPa being typical. From here it passes through a flow control valve and a visual flow display 34 e.g. a rotameter. Beyond this the gas, now at just above ambient pressure, is joined by a similar flow of $N_2O$. The source of $N_2O$ is also similar, high pressure supply 35, gas regulator 36, control valve and visual flow display 37. In addition the conducting pipe divides into two after the regulator 36 and the second conducting pathway bypasses the control valve and visual flow display 37. Instead it passes through a solenoid stepping valve 38 or similar electronic flow control device capable of regulating flowrate in response to electronic signals, in this case coming from the computer 39. It now rejoins the flow from the control valve and visual flow display 37 and then joins up with the $O_2$ flow mentioned at just above ambient pressure and also, in the case of divisional gas delivery systems supplying the right upper division RULD and the right middle and lower lobes division RMLD, is joined by a pipe carrying $CO_2$ whose source is similar to that of $O_2$. It derives from a high pressure supply 40, gas regulator 41, and control valve and visual gas display 42 before joining the $O_2$ and $N_2O$ gas flows at just above ambient pressure.

The combined flow now passes through anaesthetic vaporizer 43, in the case of the divisional gas delivery system LLD only, where it may pick up the vapor of a potent anaesthetic agent at a dialled percentage of the flowrate through it.

The gas mixture with contained vapor of potent anaesthetic agent if this has been added now passes past common gas outlet 50 into breathing system 51 comprising breathing tubing of wide bore 52, 53, and bag-in-a-box patient ventilator 45 equipped with gas overflow mechanism 55 designed to allow the concertina bag of the ventilator to remain gas tight while it is filling (expiration) but tripping the gas overflow mechanism 55 as soon as it is full (at the top of its stroke) such that further gas inflow after this point in time but before inspiration begins escapes from the bag as ventilator bag gas overflow 56 which has the composition of FGFgas.

When inspiration begins gas flows from the concertina bag down breathing tube 53 of wide bore into non-breathing inflating valve 54, down patient connection 57 and independent-part of triple lumen tube 58 (consisting of one of independent-tube part of right upper lumen 9, of right middle and lower lobes lumen 10 or of left lung lumen 11).

From here the inspiration passes into the appropriate alveolar volume division where gas exchange takes place.

While the inspiratory gas is flowing toward non-rebreathing inflating valve 54 there is added an inflow of marker gas (1) to inspiratory gas at a steady flowrate 59. The inspiratory gas passes forward a sufficient distance for radial mixing to occur and is then sampled at a constant flowrate at sampling point, inspiratory gas (1st division) 60 which carries it to a solenoid (not shown) of solenoid bank (1).

Solenoid bank (1) is a solenoid bank consisting of three solenoids passing FGFgas from each of the three divisions to gas analyser 49.

(Inspiratory gas is also sampled as it passes down patient connection 57 but this sampling is not used for fear of contamination with expiratory gas which might fail to pass non-rebreathing inflating valve 54.)

Expiratory gas then passes back the same way as far as non-rebreathing inflating valve 54. On its way it is sampled for the purpose of determining individual gas concentrations present at the end of the breath at sampling point, inspiratory and expiratory gas (1st division) 61. The sample stream passes to a solenoid which is shown of solenoid bank (2) 44. This solenoid bank consists of three solenoids passing inspiratory and expiratory gas from each of the three divisions to gas analyser 49.

Solenoids of the second solenoid bank, 44, which is shown, pass inspiratory or expiratory gas along sampling lines 61, 46 and 47 of the three divisions. Finally solenoids of the third solenoid bank, solenoid bank (3), also not show, pass EXHgas from sampling point expiratory gas 63 of each of the three divisions, to gas analyser 49.

After passing non-rebreathing inflating valve 54 it becomes gas discharged from patient, 40, and has the composition of EXHgas which receives inflow of marker gas (2) 62. This is sampled as before, this time to a solenoid of solenoid bank (3) which is not shown. It is sampled at sampling point, expiratory gas (1st division) 63.

It is important that non-rebreathing inflating valve 54 be of demonstrable efficiency in its construction. Other makes of these valves, e.g. Ruben's valves were leaky and not suitable. Efficiency is important because retrograde flow leads to inaccuracy due to double sampling.

Solenoids of solenoid banks (1), (2) and (3) open in rotation and close at the same moment the next solenoid opens so that gas flow through the analyser is continuous.

The gas analyser should be a rapid gas analyser capable of defining the expiratory wave form.

The solenoids are controlled by computer 39 through electrical connections 64–72 inclusive. Gas analyser signals are sent to the computer through analyser-to-computer-lead 73.

Gas discharged from gas analyser is lost from the system for most analysers and must be accounted for as a spurious component of uptake in the case of inspiratory gas sampled from the breathing system, 51, and of inspiratory and expiratory gas sampled from patient connection 57. In the case of expiratory gas sampled from gas discharged from patient, 40, the loss of gas does not need to be accounted for.

The whole operation of the system is conducted both manually and by operation of the computer 39. In an example of the operation of the apparatus shown in FIG. 3 the right upper lobe division, RUD 4, is ventilated initially with a gas mixture containing 79% $N_2O$, 14% $O_2$ and 7% $CO_2$.

The left lung division, LLD 8, is ventilated initially with 100% $O_2$ to which a potent anaesthetic agent vapor (e.g. isoflurane) has been added by the anaesthetic vaporizer 43 to produce a correct level of anaesthesia. Its ventilation has been adjusted to produce an end-tidal value ($F_{ETCO_2LLD}$) of 0.05 to 0.055. The ventilation is monitored by the system operator (in general, the anaesthetist). The ventilation of the RUD 4 is then set at a level of ¼ of the level of ventilation of the LLD 8.

The right middle and lower lobe division 6 is ventilated initially with 0% $N_2O$, 93% $O_2$ and 7% $CO_2$. Its ventilation is set at a level of ¾ of the level of ventilation of the LLD 8.

After a period of five to ten minutes the following may be done.

From the inspired and end-tidal concentrations of $N_2O$ in the RUD 4 ($F_{IN_2ORUD}$ and $F_{ETN_2ORUD}$) the inspired to end tidal difference is calculated. The same is done in the RMLD 6. This difference is called the $I_{ETDRUD}$ and the $I_{ETDRMLD}$. Thus:

$$F_{IN_2ORUD} - F_{ETN_2ORUD} = I_{ETDRUD}$$

$$F_{IN_2ORMLD} - F_{ETN_2ORMLD} = I_{ETDRMLD}$$

If $I_{ETDRUD}$ is negative in value the flow of $N_2O$ from its gas delivery system (1) is reduced by the solenoid stepping valve (3). The degree of reduction is related to the type of breathing system. The preferred type is a non-rebreathing system. In this case the degree of reduction is calculated, according to percent reduction of $N_2O$ desired, by a formula:

$$\text{reduction in } \dot{V}_{FGFN_2ORUD} = \frac{\% \text{ reduction desired} \times 0.01}{\text{current } F_{IN_2ORUD} \times \dot{V}_{FGFN_2ORUD}}$$

where $\dot{V}_{FGFN_2ORUD}$ is the current fresh gas flowrate of $N_2O$ in the RUD being delivered by the gas delivery system.

The percent reduction desired is the absolute value of $I_{ETDRUD}$.

After allowing a period (for stabilization of the new $I_{ETD}$ of up to a minute) the new $I_{ETD}$ is evaluated. Stabilization may not actually occur if either $F\bar{v}_{N_2O}$ or $\dot{Q}_c$ are continuing to change but evaluation of the new $I_{ETD}$ should still be done. On the basis of this, further adjustment of $\dot{V}_{FGFN_2ORUD}$ should be made in a similar way. If $I_{ETDRUD}$ is positive, $\dot{V}_{FGFN_2ORUD}$ should be adjusted back again, by increasing $\dot{V}FGFN_{2ORUD}$ similarly, but it should be adjusted to increase $F_{IN_2ORUD}$ above its initial value of 79%.

If $I_{ETDRUD}$ is positive and $F_{IN_2ORUD}$=79% balanced uptake in the RUD($I_{ETDRUD}$=0) can be obtained by raising $N_2O$) flow to the RMLD until $I_{ETDRUD}$ is equal to 0.

This process may disturb the balance in the RUD and some back and forth tracking may be necessary between $N_2O$ flow adjustment to the RMLD and to the RUD.

Small adjustments to the $\dot{V}_{FGFN_2ORUD}$ will be more responsive in altering $I_{ETDRUD}$ than equal increments or decreases of $\dot{V}_{FGFN_2ORMLD}$ will in altering $I_{ETDRMLD}$ because of the mathematical relationship.

Furthermore because the RUD is the smallest division adjustments to it will least disturb the value of $F\bar{v}_{N_2O}$. As s uch disturbance may take some minutes to manifest itself fully it is preferable as a matter of policy to make adjustment to the $\dot{V}_{FGF}$ first, wait for stabilisation and then make adjustment to the $\dot{V}_{FGFN_2ORMLD}$ being guided by the value of the increase in $\dot{V}_{FGN_2ORUD}$ achieved. The rise or fall of the value of $F_{AN_2ORUD}$ (end-tidal $F_{AN_2ORMLD}$ are likely to occur together but in opposite directions after the initial stabilisation because they are most likely to be caused by a change in cardiac output or a change in whole body $O_2$ uptake. The ratio of the rise in $\dot{V}_{FGFN_2ORMLD}$: rise in $\dot{V}_{FGFN_2ORUD}$ is expected to be 15–20 over most of the range of $F_{AN_2ORMLD}$ and $F_{AN_2ORUD}$ values (which are 0–65 and 65–80 respectively approximately).

The strategy of adjusting the $\dot{V}_{FGFN_2ORUD}$ first can be computerised although probably it remains best to make the initial stabilisation manually. To this end manual adjustment under visual control is made available but a parallel system of finer control by a computer through a solenoid stepping valve is also provided in the preferred system.

The initial process of adjustment of the two balance values to be selected, the higher one in the RUD and the lower one in the RMLD gives the system operator the choice over a range of $F\bar{v}_{N_2O}$, higher $F\bar{v}_{N_2O}$ values causing them to be closer together, lower ones farther apart.

The value of $F\bar{v}_{N_2O}$ that determines this can be set independently by allowing a flow of $N_2O$ into the left lung from its gas delivery system (positive value of $\dot{V}_{FGFN_2OLLD}$). The choice of $F\bar{v}_{N_2O}$ to be selected is a matter of judgment.

The computer can be programmed to set a particular value of $F\bar{v}_{N_2O}$, a parameter which can be calculated from $Q_c$ once it is first known. It can be programmed to track and defend this value through adjustment of $\dot{V}_{FGFN_2OLLD}$, and it can be programmed to defend the balanced state in both the RUD and the RMLD by adjustments to both the $\dot{V}_{FGFN_2ORUD}$ and $\dot{V}_{FGFN_2ORMLD}$ when imbalance spontaneously appears.

The output of the computer, 39, to visual display 74, printout 75 or RS232 interface 76 will go to other electronic devices, and/or any other useful output modality and will also be capable of carrying information concerning any of the values of the various parameter variables observed by the measuring instruments or calculated from their readings and/or other data stored in its memory or communicated to it from other sources, e.g. manual input or RS232 communication from other electronic devices.

Numerical Example

Suppose that relevant variables listed below posses the stated plausible values:

| Inspired $F_{N_2O}$, | left = 0.8 | Inspired $F_{N_2O}$, | right = 0 |
|---|---|---|---|
| Alveolar ventilation | left = 2 L/m | Alveolar ventilation | right = 2 L/m |
| | $\dot{Q}_cL = 2.5 \, L/m$ | | $\dot{Q}_cR = 2.5 \, L/m$ |
| | $F\bar{v}_{N_2O} = 0.4$ | | |

(The value of $Fv_{N_2O}$ lies midway between inspired $F_{N_2O}$ on the left and inspired $F_{N_2O}$ on the right if sufficient time has passed since the induction of anaesthesia for saturation of the body tissues with $N_2O$.)

$\lambda N_2 O = 0.5 \quad \dot{U}_{O_2R} = 0.125 \, L/m$ $\dot{U}_{O_2L} = 0.125 \, L/m$ The alveolar $F_{N_2O}$ on the two sides can now be calculated. Alveolar gas can be considered to be formed by the direct mixture of two streams of $N_2O$-containing fluid. (This is true because the alveolo-capillary membrane separating blood from gas is freely permeable to $N_2O$.) Let a mass balance equation be set up such that the mass of $N_2O$ carried into each lung is equal to the mass carried away. Then:

$$F_{IN_2OL} \cdot \dot{V}_{AIL} + F v_{N_2OL} \cdot \dot{Q}_{cL} \cdot \lambda_{N_2O} = F_{AN_2OL} \cdot (\dot{V}_{AIL} + \dot{Q}_{cL} \cdot \lambda_{N_2O})$$

where $F_{IN_2OL}$ is the left inspired $F_{N_2O}$ and $V_{AIL}$ is the left alveolar ventilation.

$$\therefore F_{AN_2OL} = \frac{F_{IN_2OL} \cdot \dot{V}_{AIL} + F \bar{v}_{N_2O} \cdot \dot{Q}_{cL} \cdot \lambda_{N_2O}}{\dot{V}_{AIL} + \dot{Q}_{cL} \cdot \lambda_{N_2O}}$$

Similarly:

$$F_{AN_2OR} = \frac{F_{IN_2OR} \cdot \dot{V}_{AIR} + F \bar{v}_{N_2O} \cdot \dot{Q}_{cR} \cdot \lambda_{N_2O}}{\dot{V}_{AIR} + \dot{Q}_{cR} \cdot \lambda_{N_2O}}$$

$\dot{U}_{N2OL}$ and $\dot{U}_{N2OL}$ are calculated from the equations:

$$\dot{U}N_{2OL} = (F_{AN_2OL} - F v_{N_2O}) \cdot \dot{Q}_{cL} \cdot \lambda_{N_2O}$$

and $$\dot{U}_{N_2OR} = (F_{AN_2OR} - F v_{N_2O}) \cdot \dot{Q}_{cR} \cdot \lambda_{N_2O}$$

Using the stated values for the variables on the right:

$\dot{U}_{N_2OL} = 0.307692 \, L/m$ $\dot{U}_{N_2OR} = 0.307692 \, L/m$

Thus expected uptake rates in normal human subjects in health will approximate 300 mls/min. (When tissues are not saturated with $N_2O$, uptake from the left will be somewhat increased. Output from the right will be somewhat decreased. The uptake rate at the start will be approximately 615 mls/min on the left side with little output on the right. The uptake rate at ten minutes is approximately 340 mls/minute and the right output is approximately 280 mls/minute. Thereafter uptake declines more slowly. At one and a half hours left uptake is only 25 mls per minute greater than right output. Tissue uptake need-not be considered a serious cause of any loss in precision of measurement of uptake and output.)

The calculated values for $F_{AN_2OL}$ and $F_{AN_2OR}$ after tissue saturation are:

$F_{AN_2OL} = 0.646154$ $F_{AN_2OR} = 0.153846$

The cardiac output equation derived previously is:

$$\dot{Q}_c = \frac{\dot{U}_{N_2OL}\left(1 + \frac{\dot{U}_{O_2R}}{\dot{U}_{O_2L}}\right) - \dot{U}_{N_2OR}\left(1 + \frac{\dot{U}_{O_2L}}{\dot{U}_{O_2R}}\right)}{\lambda(F_{AN_2OL} - F_{AN_2OR})}$$

Inserting the values for the variables into this equation:

$$\dot{Q}_c = \frac{0.307692\left(1 + \frac{0.125}{0.125}\right) - (-0.307692)\left(1 + \frac{0.125}{0.125}\right)}{0.5(0.646154 - 0.153846)}$$

$$= \frac{2 \times 0.615384}{0.5 \times 0.492308}$$

$$= 5.00 \, L/min.$$

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Those skilled in the art will appreciate that the invention described herein is susceptible to variations and modifications other than those specifically described. It is to be understood that the invention includes all such variations and modifications. The invention also includes all of the steps and features referred to or indicated in this specification, individually or collectively, and any and all combinations of any two or more of said steps or features.

What is claimed is:

1. A method for measuring the pulmonary blood flow in a subject including:
   isolating two or more divisions of the respiratory system, said divisions comprising the complete gas exchanging part of said respiratory system,
   ventilating each said division with a separate gas mixture, at least one of said gas mixtures including an inert soluble gas,
   determining uptake of inert soluble gas in at least two of said divisions,
   determining uptake of oxygen in each of said divisions,
   determining end tidal concentration of inert soluble gas in at least two of said divisions, and
   calculating pulmonary blood flow from determined values of uptake and end tidal concentration of inert soluble gas, and uptake of oxygen.

2. A method according to claim 1 wherein two divisions of the respiratory system are isolated.

3. A method according to claim 2 wherein said two divisions comprise the left and right lungs respectively.

4. A method according to claim 1 wherein said inert soluble gas comprises nitrous oxide.

5. A method according to claim 1 wherein at least one of said gas mixtures comprises two or more inert soluble gases.

6. A method according to claim 1 wherein said inert soluble gas comprises sevoflurane and/or desflurane.

7. A method according to claim 1 wherein at least one of said gas mixtures comprises nitrous oxide and sevoflurane or desflurane.

8. A method according to claim 1 wherein subject is under anaesthetic.

9. A method according to claim 1 wherein said uptakes of inert soluble gas is determined using an inert insoluble gas as a marker gas.

10. A method according to claim 1 wherein one gas mixture comprises 60% to 80% by volume of inert soluble gas and the other gas mixture comprises 0 to 20% inert soluble gas.

11. A method according to claim 10 wherein said other gas mixture contains none of said inert soluble gas.

12. A method according to claim 1 wherein one gas mixture comprises inert soluble gas and the other gas mixture comprises none of said inert soluble gas.

13. A method according to claim 1 wherein three divisions of the expiratory system are isolated.

14. A method according to claim 13 wherein two of said divisions are ventilated with gas mixtures which are substantially balanced with respect to said inert soluble gas, the concentration of inert soluble gas in each of two divisions being different from each other, and said third division is ventilated with a gas mixture which is unbalanced with respect to inert soluble gas.

15. A method according to claim 14 wherein said two divisions are substantially balanced with respect to inert soluble gas and carbon dioxide.

16. A method according to claim 14 wherein the balanced concentrations of inert soluble gas in said two divisions is determined by:
  determining expired tidal concentration of inert soluble gas in said third division,
  estimating cardiac output of subject,
  calculating approximate higher and lower balanced concentrations of inert soluble gas from estimate of cardiac output and end tidal concentration of inert soluble gas in said third division,
  adjusting concentration of inert soluble gas in said two divisions to said approximate higher and lower balanced concentration,
  adjusting concentration of inert soluble gas, in each of said two divisions until substantial balance is attained,
  calculating pulmonary blood flow while gas mixtures provided to said two divisions is substantially balanced with respect to inert soluble gas.

17. A method according to claim 14 wherein said third division is supplied with a gas mixture containing none of said inert soluble gas.

18. A method according to claim 1 or claim 14 wherein the pulmonary blood flow is calculated at a plurality of time intervals.

19. A method according to claim 16 wherein the pulmonary blood flow is calculated at a plurality of time intervals and the balanced concentration of inert soluble gas in said two divisions is readjusted in response to changes in cardiac output or total oxygen uptake.

20. Apparatus for measuring pulmonary blood flow in a subject including:
  a multi-lumen cuffed endobronchial catheter adapted to allow separate gas mixtures to be provided to two or more isolated divisions of the respiratory system of the subject, said isolated divisions comprising the complete gas exchanging part of said respiratory system,
  two or more breathing systems for supplying different mixtures to each lumen of said multi-lumen catheter at the same rate and the same total pressure,
  two or more gas delivery systems for providing gas mixtures to said two or more breathing systems;
  sampling means for sampling (i) inspired and expired gas in each division and/or (ii) the fresh flow gas and the exhaust gas of each division, and
  gas analyser for determining concentrations of gases in said samples,
  flow determining means for determining flow rates of (i) said inspired and expired gas and/or (ii) said fresh flow gas and exhaust gas determined, and
  processing system for calculating pulmonary blood flow from said concentrations and flow rates.

21. Apparatus according to claim 20 further including a sampling means for sampling gas composition delivered to breathing system from gas delivery system.

22. Apparatus according to claim 20 further including a sampling means for sampling exhaust gas from breathing system.

23. Apparatus according to claim 20 wherein multi-lumen cuffed endobronchial catheter has two or three lumens.

24. A triple lumen, cuffed endobronchial catheter for providing separate gas mixtures to each of three separate divisions of the respiratory system of a subject, said three divisions comprising the complete gas exchanging part of said respiratory system, said catheter comprising:
  a primary tube having three lumens adapted to be inserted within the trachea of a subject, each of said lumens opening at a top end thereof into a connector tube adapted to be connected to a breathing system, and opening at a bottom end thereof into an outlet for delivering a gas mixture to one of said divisions,
  one or more inflatable cuffs located about said primary tube and/or said outlets adapted to form seals within the respiratory system such that each outlet is capable of delivering a gas mixture to one of said three separate divisions in isolation from each of the other divisions.

25. A triple lumen cuffed endobronchial catheter according to claim 24 having a first inflatable cuff located about the primary tube and above the outlets which is adapted to form a first seal within the trachea.

26. A triple lumen cuffed endobronchial catheter according to claim 25 having a second inflatable cuff located between the first and third outlets and about the second outlet for forming a second seal in the right bronchus and a third seal in the hyparterial bronchus, the third seal allowing the third outlet to provide a gas mixture to the middle and lower lobes of the right lung and the second seal allowing the second outlet to provide a gas mixture to the upper lobe of the right lung.

27. A triple lumen cuffed endobronchial catheter according to claim 25 having a second inflatable cuff located between the first and third outlets and about the second outlet for forming a second seal in the left bronchus and a third seal in the hyparterial bronchus, the third seal allowing the third outlet to provide a gas mixture to the lower lobe of the left lung and the second seal allowing the second outlet to provide a gas mixture to the upper lobe of the left lung.

* * * * *